US010184104B2

(12) United States Patent
Lianides et al.

(10) Patent No.: US 10,184,104 B2
(45) Date of Patent: Jan. 22, 2019

(54) AUTOMATED SYSTEM FOR CULTIVATING TRANSGENIC C. ELEGANS

(71) Applicants: Alexander Lee Lianides, Aliso Viejo, CA (US); Christopher Lee Lianides, Aliso Viejo, CA (US)

(72) Inventors: Alexander Lee Lianides, Aliso Viejo, CA (US); Christopher Lee Lianides, Aliso Viejo, CA (US)

( * ) Notice: Subject to any disclaimer, the term of this patent is extended or adjusted under 35 U.S.C. 154(b) by 209 days.

(21) Appl. No.: 15/292,084

(22) Filed: Oct. 12, 2016

(65) Prior Publication Data

US 2017/0145373 A1     May 25, 2017

Related U.S. Application Data

(60) Provisional application No. 62/257,703, filed on Nov. 19, 2015.

(51) Int. Cl.
| | |
|---|---|
| *C12M 1/36* | (2006.01) |
| *C12M 3/00* | (2006.01) |
| *C12M 1/12* | (2006.01) |
| *C12M 1/32* | (2006.01) |
| *C12M 3/06* | (2006.01) |
| *C12M 1/34* | (2006.01) |
| *C12N 5/07* | (2010.01) |
| *C12M 1/26* | (2006.01) |
| *C12M 1/00* | (2006.01) |

(52) U.S. Cl.
CPC ............ *C12M 41/48* (2013.01); *C12M 23/12* (2013.01); *C12M 23/38* (2013.01); *C12M 23/42* (2013.01); *C12M 23/48* (2013.01); *C12M 23/50* (2013.01); *C12M 25/04* (2013.01); *C12M 25/06* (2013.01); *C12M 27/16* (2013.01); *C12M 33/07* (2013.01); *C12M 41/42* (2013.01); *C12M 41/44* (2013.01); *C12N 5/0601* (2013.01)

(58) Field of Classification Search
USPC ............ 422/62–68.1, 552, 554; 435/42–91.1
See application file for complete search history.

(56) References Cited

U.S. PATENT DOCUMENTS 9,028,752 B2* 5/2015 Malin ................... C12M 23/10
                                                                   422/63
2004/0073956 A1* 4/2004 Verwaerde ......... A01K 67/0333
                                                                800/3

(Continued)

OTHER PUBLICATIONS

Squiban, B., Belougne, J., Ewbank, J., Zugasti, O. Quantitative and Automated High-throughput Genome-wide RNAi Screens in C. elegans. J. Vis. Exp. (60), e3448, doi:10.3791/3448 (2012). (Year: 2012).*
Solis, G.M., Petrascheck, M. Measuring Caenorhabditis elegans Life Span in 96 Well Microtiter Plates. J. Vis. Exp. (49), e2496, doi:10.3791/2496 (2011). (Year: 2011).*
O'Rouke et al. P.A. Clemons et al. (eds.), Cell-Based Assays for High-Throughput Screening, Methods in Molecular Biology, vol. 486 © Humana Press, a part of Springer Science + Business Media, LLC 2009 DOI: 10.1007/978-1-60327-545-3_1 (Year: 2009).*

(Continued)

*Primary Examiner* — Nina Bhat

(57) ABSTRACT

The present invention provides a self-draining well plate cassette and an automated system for cultivating *C. elegans* comprising a housing, a well plate assembly having at least two of the self-draining well plate cassettes, a liquid dispensing assembly operated by a first three axes positioner, a wash and imaging assembly operated by a second three axis positioner, a reagent assembly, a pipette tip holder, and a controller. The present invention further provides a method of using the above-described system to cultivate *C. elegans*.

17 Claims, 14 Drawing Sheets

(56) References Cited

U.S. PATENT DOCUMENTS

| | | | |
|---|---|---|---|
| 2006/0050376 A1* | 3/2006 | Houston | G02B 21/16 359/392 |
| 2006/0191023 A1* | 8/2006 | Gill | A01K 67/033 800/3 |
| 2010/0126286 A1* | 5/2010 | Self | G01N 35/04 73/863.81 |
| 2010/0263599 A1* | 10/2010 | Yanik | A61K 49/0008 119/216 |
| 2011/0154510 A1* | 6/2011 | Pak | C07K 14/47 800/3 |
| 2011/0269226 A1* | 11/2011 | Van Noort | C12M 23/16 435/325 |
| 2015/0273469 A1* | 10/2015 | Reed | B01L 3/50851 141/1 |
| 2017/0107470 A1* | 4/2017 | Fang-Yen | B01L 3/5085 |
| 2017/0142945 A1 | 5/2017 | Demetrescu et al. | |

OTHER PUBLICATIONS

Ragaraju et al. "High-throughput Small-Molecule Screen in Caenorhabditis elegans", 2014; P.A. Clemons et al. (eds.), Cell-Based Assays for High-Throughput Screening, Methods in Molecular Biology, vol. 486 © Humana Press, a part of Springer Science + Business Media, LLC 2009 DOI: 10.1007/978-1-60327-5 (Year: 2014).*

Fitzgerald et al. "A transfer-less, multi-well liquid culture feeding system for screen smal molecules that affect the longevity of Caenorhabditis elegans", www.Bitotechniques.com, vol. 47/No. 6/2009 (Year: 2009).*

Demetrescu, Anthony, et al., First FRC 3476 Worm Washer Research Robot Project, http://teamcodeorange.com/uci.php, Nov. 2, 2015; 9 pages, Code Orange Robotics, Inc., Irvine.

* cited by examiner

AUTOMATED SYSTEM FOR CULTIVATING TRANSGENIC *C. ELEGANS*

CLAIM OF BENEFIT OF FILING DATE

This application claims the benefit of U.S. Provisional Application Ser. No. 62/257,703 titled: "Automated System for Cultivating Transgenic *C. Elegans*:" filed on Nov. 19, 2015.

FIELD OF INVENTION

The present invention relates to an automated system for cultivating transgenic *Caenorhabditis elegans* ("*C. elegans*").

BACKGROUND OF THE INVENTION

*C. elegans* is a nematode (roundworm) that is known as the first multicellular eukaryote to have its entire genome sequenced. It has approximately 19-20,000 protein-encoding genes incorporated in 100,258,171 base pairs of DNA. It has physiological systems found in other animals such as mice and humans. *C. elegans* is ideal for transgenic experimentation because it is sufficiently small in size and reproduces rapidly allowing it to be raised in large numbers in wells of a standard well plate containing its bacterial food source such as *E. coli*. It is transparent so its every cell is visible under the microscope. Scientists can view its entire 2-3 weeks life cycle from the fertilized egg to the adult worm. In 1998, it was discovered that injection of double stranded RNA into *C. elegans* leads to interference. Thereafter, it was discovered that feeding *C. elegans* with bacteria engineered to produce double stranded RNA also could induce a robust RNA interference response. These discoveries and the knowledge of the complete genomic sequence of *C. elegans* made it possible to conduct rapid study and experimentation of gene function, both on a single gene level and on a global level. See Worm Book at http://www.wormbook.org.

In light of the foregoing, it is not surprising that *C. elegans* is often used in transgenic research worldwide. Unfortunately, the cultivation of transgenic *C. elegans* is labor intensive requiring daily feeding, cleaning, and imaging. In most labs, these steps are manually processed by lab technicians which limits throughput. The present invention overcomes this throughput problem by providing an automated system for cultivating transgenic *C. elegans*. The system provides significantly higher throughput while reduces the number of man-hours required to cultivate transgenic *C. elegans*.

DETAILED DESCRIPTION OF THE DRAWINGS

The features and inventive aspects of the present invention will become more apparent upon reading the following detailed description, claims, and drawings, of which the following is a brief description:

DETAILED DESCRIPTION OF THE INVENTION

Figure 1:
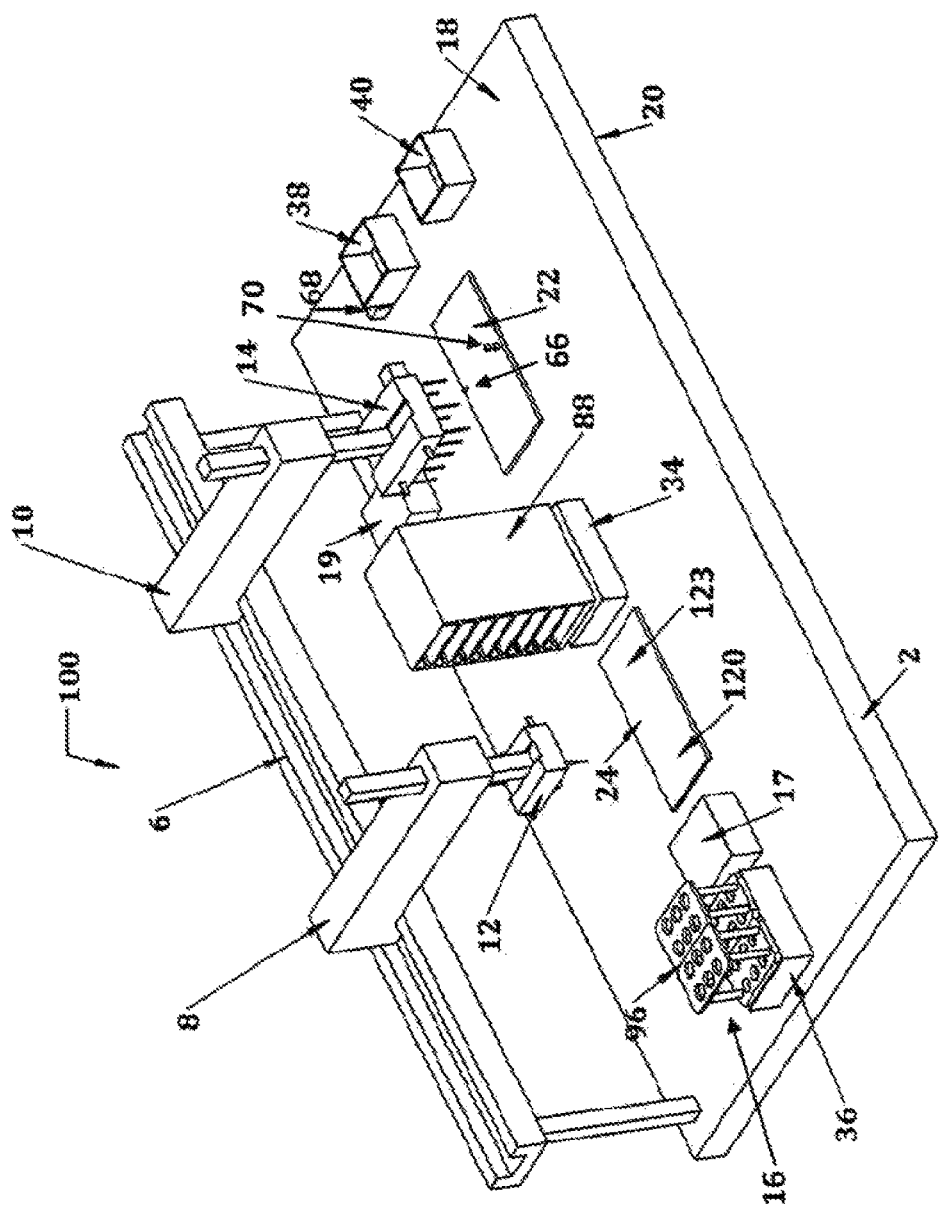
FIG. 1 is a perspective view of a non-limiting embodiment of a robotic system for cultivating transgenic *C. elegans* in accordance to the principles of the present invention.
Figure 2:
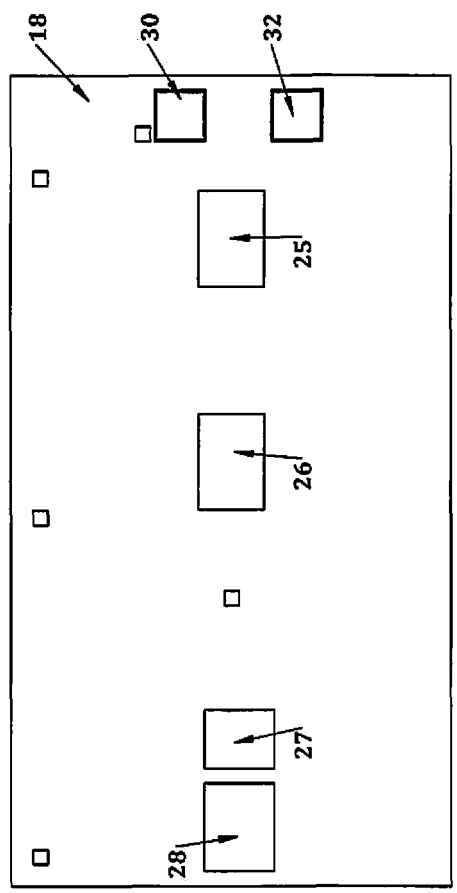
FIG. 2 illustrates a top view of the base plate of the system of FIG. 1.

Referring to FIGS. 1-2, and 11-12, the present invention provides an automated system 100 for cultivating transgenic *C. elegans* comprising a housing 2, a well plate assembly 4, a robot 6 having two three-axes arms 8, 10, a liquid dispensing assembly 12, a wash and imaging assembly 14, a reagent assembly 16, a pipette tip holder 17, and a controller 19. The housing 2 includes a base platform 18 and a base plate 20. The robot 6 is attached to one side of the base platform 18 as shown in FIG. 1, allowing each arm (8, 10) to be movable over one-half portion of the base platform 18. The base platform 18 includes a raised washing platform 22 and a raised reagent platform 24. Five cutouts 25, 26, 28, 30, 32 are formed between the base platform 18 and the base plate 20. The cutout 26, located between the cutout 28 and the cutout 25, is used to secure an orbital shaker 34 of the well plate assembly 4. The cutout 28 is used to secure another orbital shaker 36 of the reagent assembly 16. The cutout 25 is used to secure and house the washing platform 22 and its components discussed below. Two cutouts 30, 32 located adjacent to the other side of cutout 25 are used to secure the waste container 38 and the buffer container 40.

Figure 4:
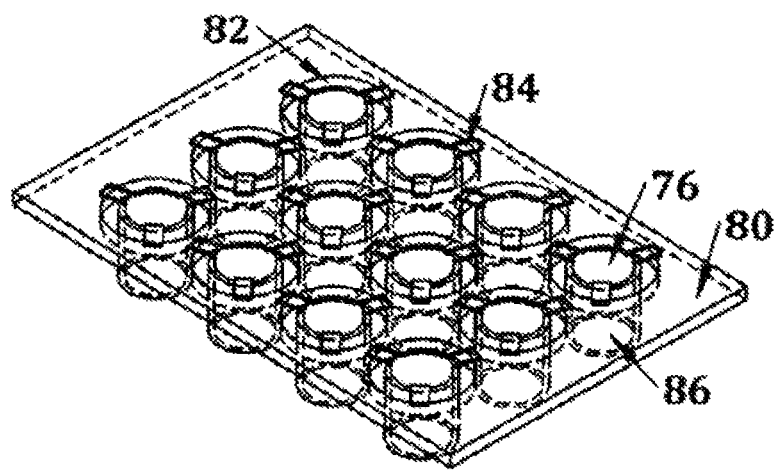
FIG. 4 illustrates a perspective view of the culture insert carrying plate and inserts shown in FIG. 3.
Figure 5:
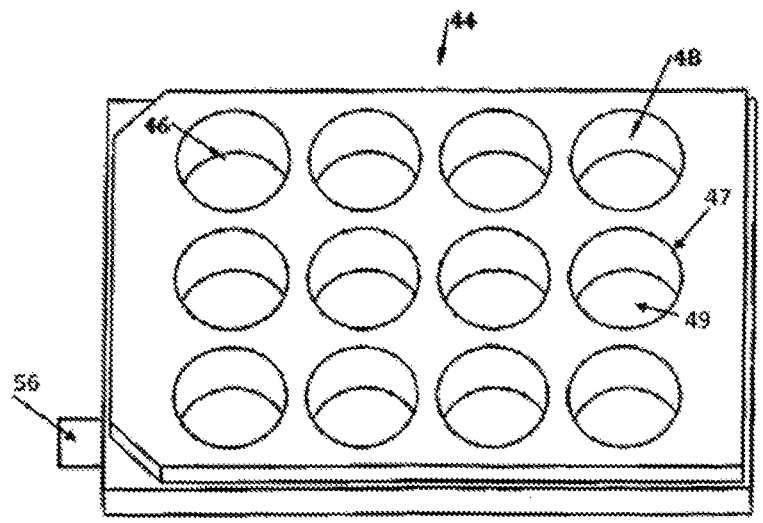
FIG. 5 illustrates a perspective view of the top plate of the well plate cassette shown in FIG. 3.

Referring to FIGS. 3-9, 11, 3A, 6A, 6B, 7A, 8A and 9A, the well plate assembly 4 includes a predetermined number of self-draining well plate cassettes 42. In the two non-limiting embodiments shown herein, the well plate assembly 4 includes eight well plate cassettes 42. Each cassette 42 includes a top plate 44 containing a predetermined number of open wells 46. Each open well 46 is formed by a continuous well wall 48 with a top opening 47 and a bottom opening 49. The well wall 48 can be in any suitable art-disclosed size and shape. For example, the well wall 48 can be an open cylinder as shown in FIG. 5, sized like the well wall of the wells of a standardized well plate. See e.g., the 12 wells (3×4) CELLSTAR Cell Culture Multiwell Plates manufactured by Greiner Bio-One located in Germany. Alternatively, the well wall 48 can be an open cylinder that tapers (either continuously or sectionally) resulting in a bottom opening 49 that has a small diameter when compared to the top opening 47 as shown in FIGS. 5B, 8A, and 9A.

Figure 6:
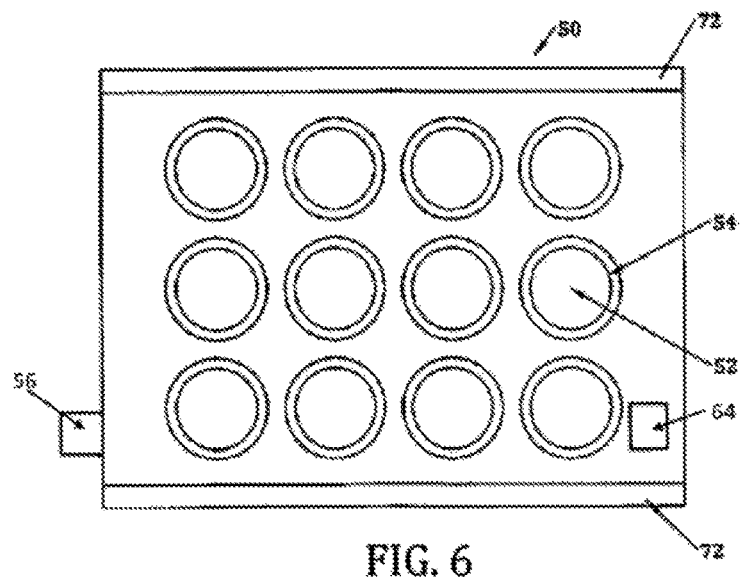
FIG. 6 illustrates a top view of the base plate of the well plate cassette shown in FIG. 3.
Figure 6A:
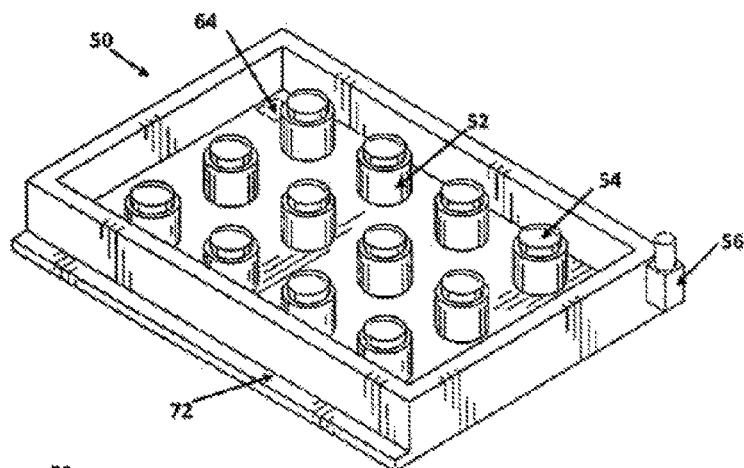
FIG. 6A illustrates a top view of the base plate of the well plate cassette shown in FIG. 3A.
Figure 6B:
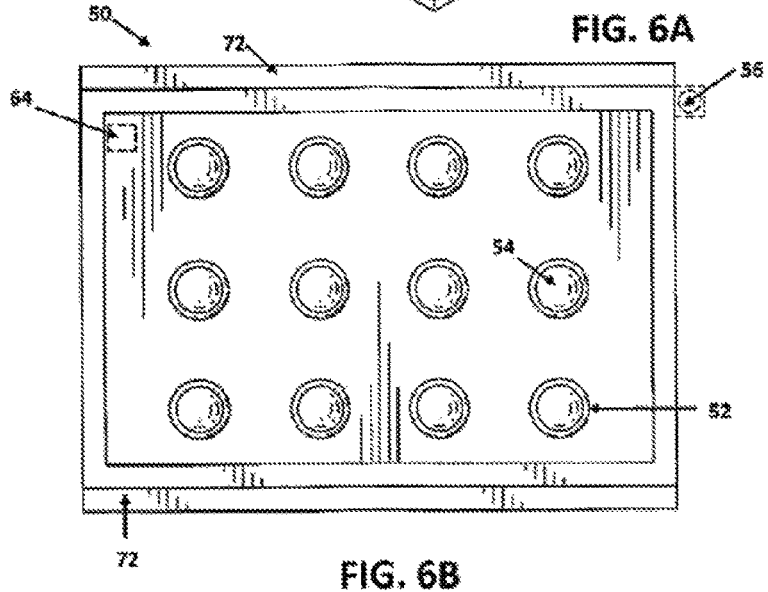
FIG. 6B illustrates a perspective view of the base plate shown in FIG. 6A.
Figure 7:
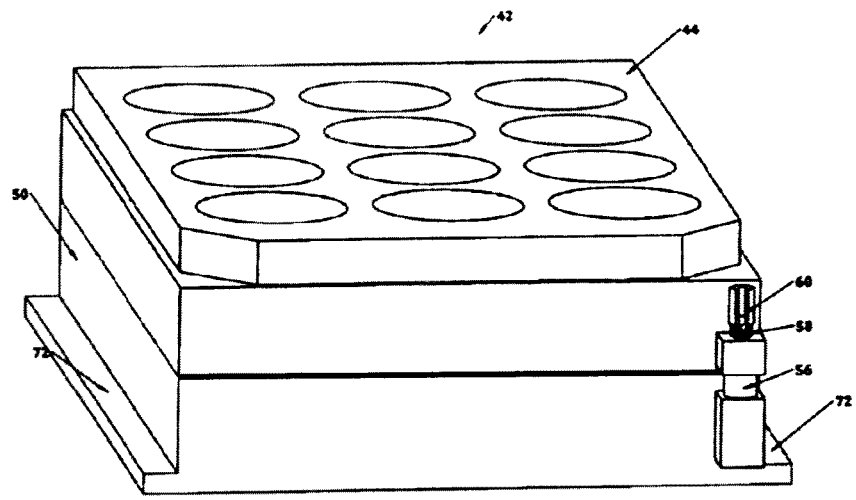
FIG. 7 illustrates a perspective view of the well plate cassette shown in FIG. 3 with the spring loaded connector.
Figure 7A:
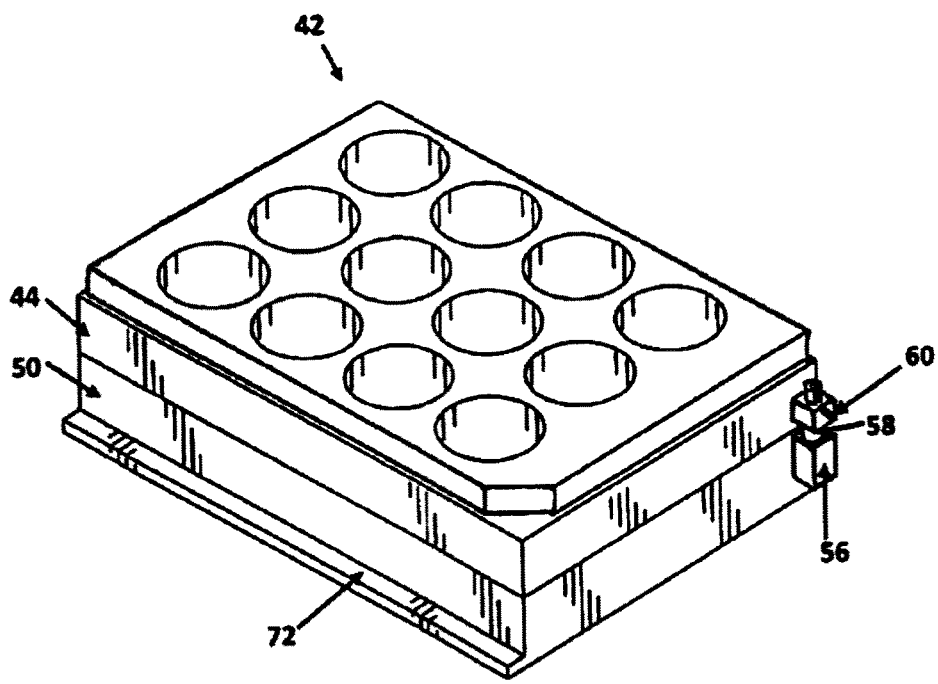
FIG. 7A illustrates a perspective view of the well plate cassette shown in FIG. 3A with the spring loaded connector.

Referring to FIGS. 3, 3A, 6, 6A and 6B, the cassette 42 further includes a base plate 50 containing multiple raised well bottoms 52 that correspond to the locations of the bottom opening 49. Each well bottom 52 includes an art-disclosed sealing feature 54 such as O-rings as shown in FIG. 6 or silicone surface as shown in FIGS. 6A-6B. The bottom opening 49 can couple with the O-rings 54 to prevent fluid leakage in various way such as (i) being placed within the O-ring 54, (ii) the O-ring 54 is placed inside the bottom opening 49, or a combination of both (e.g., using two O-rings 54—one placed inside the bottom opening 49 and one placed around the bottom opening 49).

Figure 8:
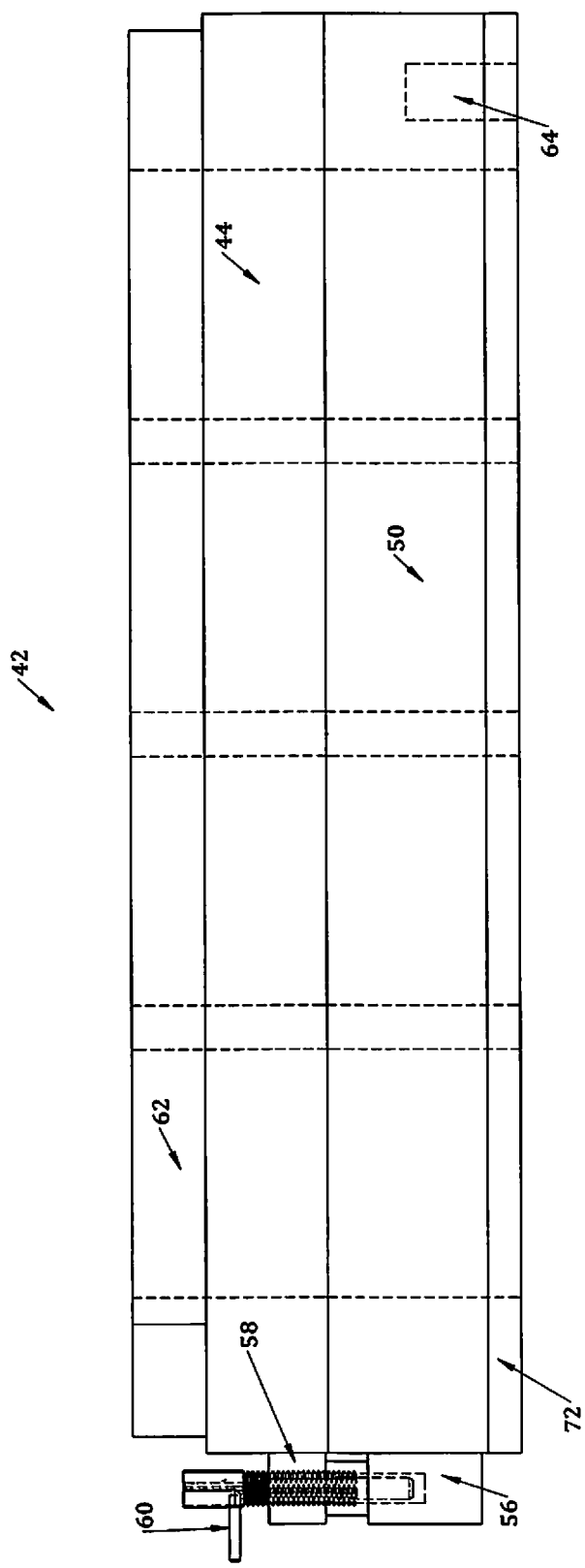
FIG. 8 illustrates a side view of the well plate cassette shown in FIG. 7 when the biasing tension spring is compressed.
Figure 8A:
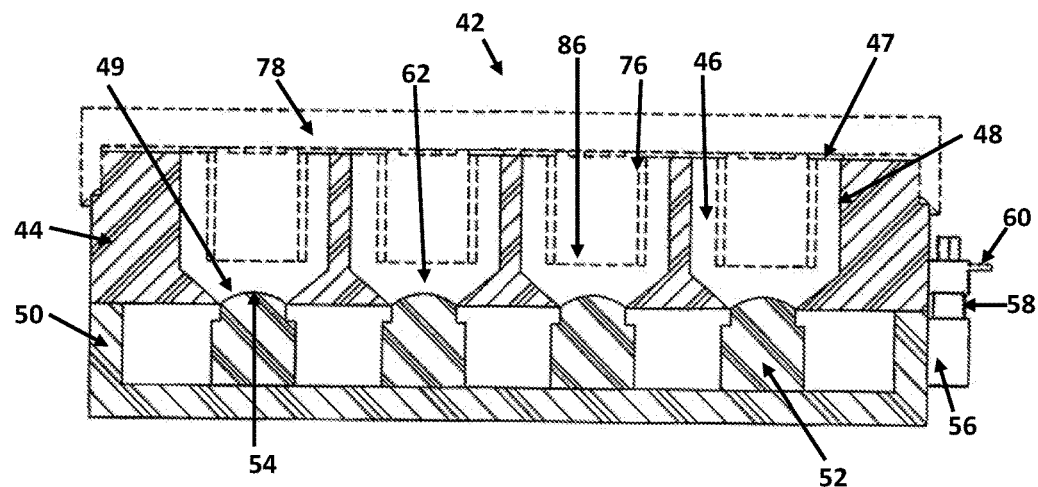
FIG. 8A illustrates a cross-sectional view of well plate cassette shown in FIG. 3A when the biasing tension spring is compressed.
Figure 9A:
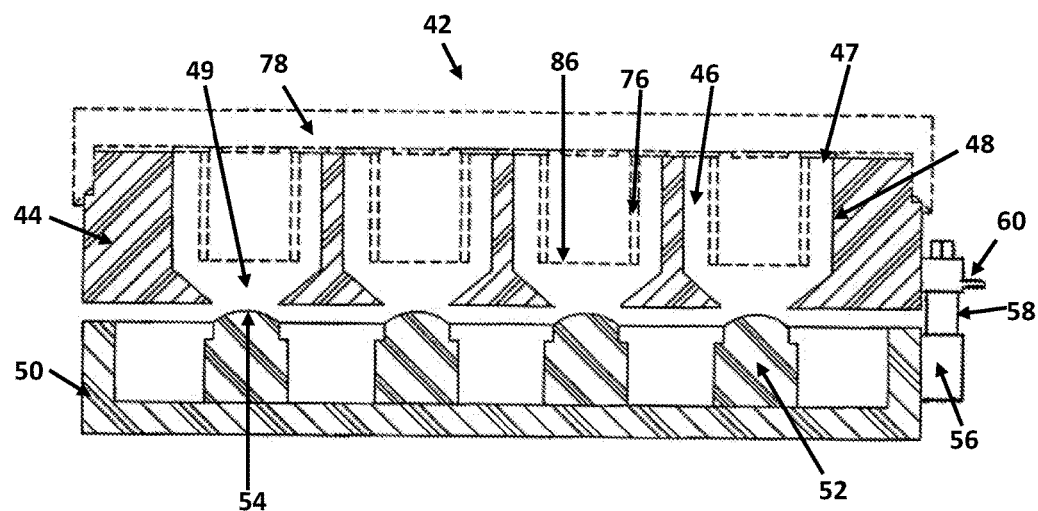
FIG. 9A illustrates a cross-sectional view of the well plate cassette shown in FIG. 3A when the biasing tension spring is extended.
Figure 9:
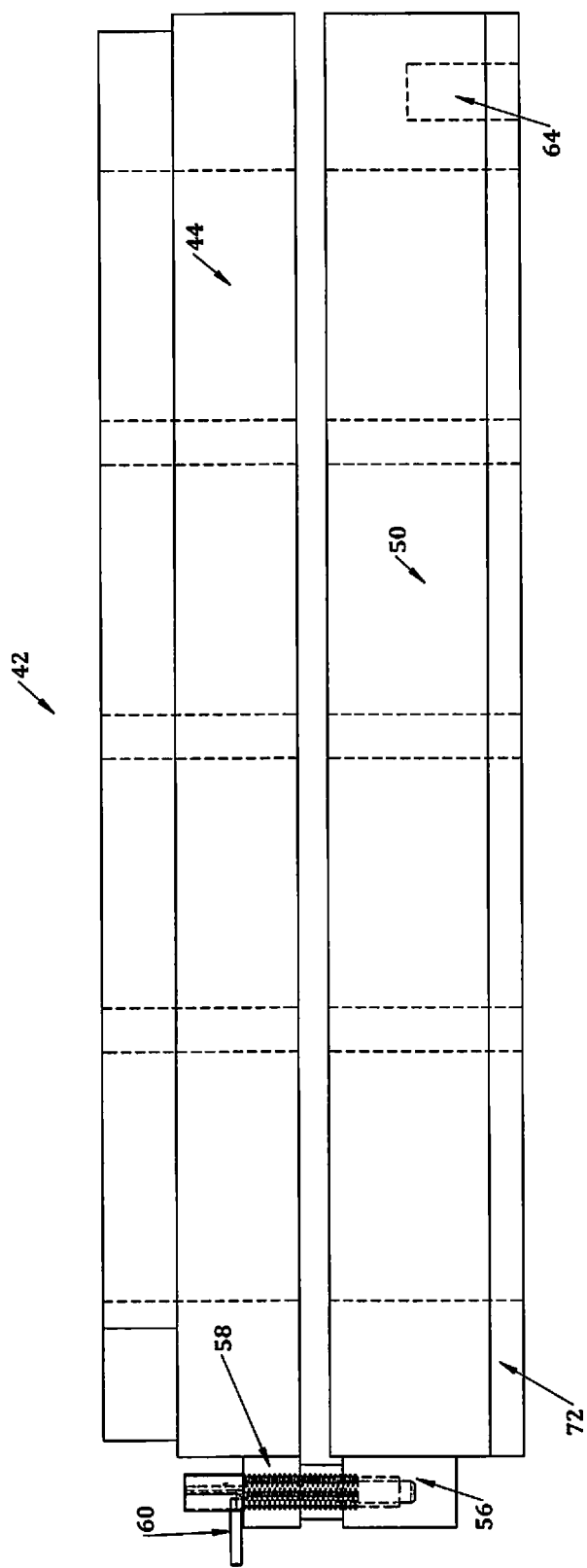
FIG. 9 illustrates a side view of the well plate cassette shown in FIG. 7 when the biasing tension spring is extended.

Referring to FIGS. 3, 5-9, 3A, 6A, 6B, 7A, 8A and 9A, a spring loaded connector 56 is attached to both the top plate 44 and the base plate 50. The spring loaded connector 56 includes a biasing tension spring 58 and a lever 60. When the lever 60 is pressed down, it (60) depresses the biasing tension spring 58 resulting in compression of the spring 58. This compression of the spring 58 causes each bottom opening 49 of the open wells 46 to couple with its corresponding well bottom 52 and the sealing feature 54 to form a sealed well 62 that can contain fluid without leakage as shown in FIGS. 8 and 8A. When the level 60 is lifted up, it (60) releases the biasing tension spring 58 resulting in the extension of the spring 58. The extension of the spring 58 causes the bottom openings 49 to decouple from their corresponding well bottoms 52 allowing fluid contained therein to leak out onto the base plate 50 as shown in FIGS. 9 and 9A.

Referring to FIGS. 1, 3A, 6, 6A, 6B, 8-10, the cassette 42 further includes a drainage valve 64 in fluid communication and attached to the base plate 50. The drainage valve 64 is designed to mate or couple with a drainage coupler 66 located on the washing platform 22. During operation, the coupler 66 is in fluid communication with the waste container 38 via a drainage conduit 68 having art-disclosed pump and tubing. When the drainage valve 64 is decoupled from the drainage coupler 66, the drainage valve 64 is designed to prevent fluid leakage from the cassette 42 and the drainage coupler 66 is designed to prevent fluid leakage from itself, the drainage conduit 68, and the waste container 30.

Figure 10:
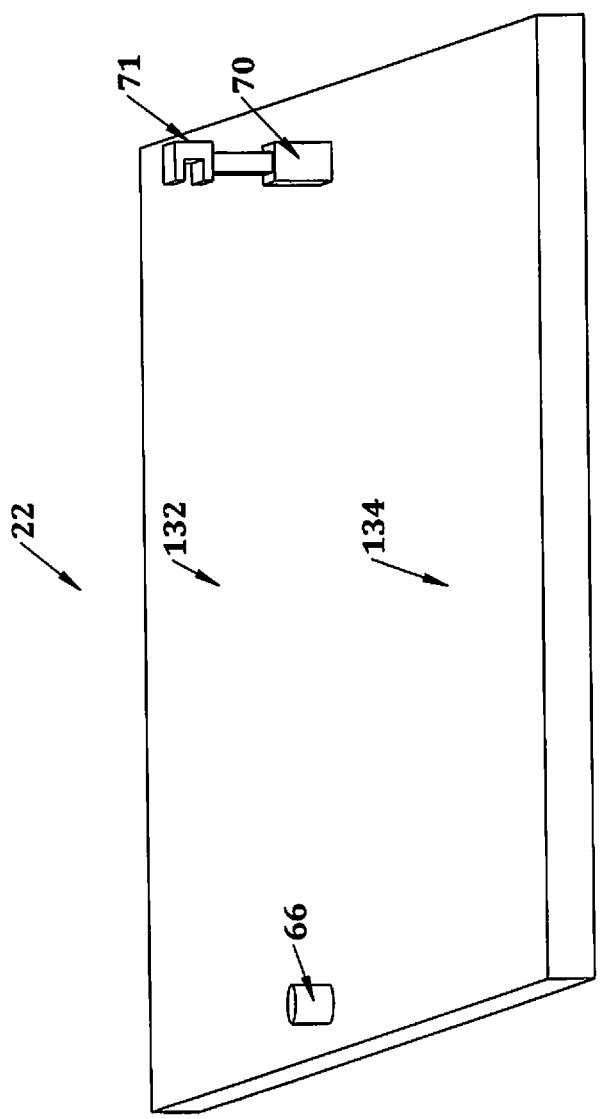
FIG. 10 is a perspective view of the washing platform of the system shown in FIG. 1.

Referring to FIG. 10, a linear actuator 70 is located on the washing platform 22 and used to move the lever 60 of the spring loaded connector 56. The linear actuator 70 includes a switch controller 71. During operation, the cassette 42 is placed onto the washing platform in a fashion that allows the level 60 to engage with the switch controller 71 and the coupling of the drainage valve 64 (female) with the drainage coupler 66 (male). When the linear actuator 70 is extended, the switch controller 71 lifts up the level 60 causing the biasing tension spring 58 to extend. Referring to FIGS. 9 and 9A, this extension of the spring 58 causes the bottom openings 49 to decouple from their corresponding well bottoms 52 which allows fluid contained therein to leak out onto the base plate 50. Since the drainage valve 64 (female) is now coupled with the drainage coupler 66 (male), fluid communication between them (64, 66) has been established so that the fluid that has leaked out onto the base plate 50 caused by the extension of the biasing tension spring 58 described above now travels from the cassette 42 to the waste container 38 through the drainage valve 64, the drainage coupler 66, and the drainage conduit 68. This design provides quick drainage of used bacteria solutions contained in the wells 62 while avoiding potential cross-contamination among the wells 62. The drainage valve 64 and the drainage coupler 66 can be any art-disclosed dry disconnect coupling devices. See e.g., U.S. Pat. No. 7,658,205.

Referring to FIGS. 8 and 8A, when the linear actuator 70 is retracted, the switch controller 71 depresses the level 60 in order to compress the biasing tension spring 58. This compression of the spring 58 causes the bottom openings 49 to couple with their corresponding the well bottoms 52 and its sealing feature 54 to form sealed wells 62 that can contain fluid without leakage. The linear actuator 70 can be any suitable art-disclosed linear actuator including but not limited to the linear actuator described in U.S. Pat. No. 8,508,168. The linear actuator 70 is controlled by the controller 19.

Figure 3:
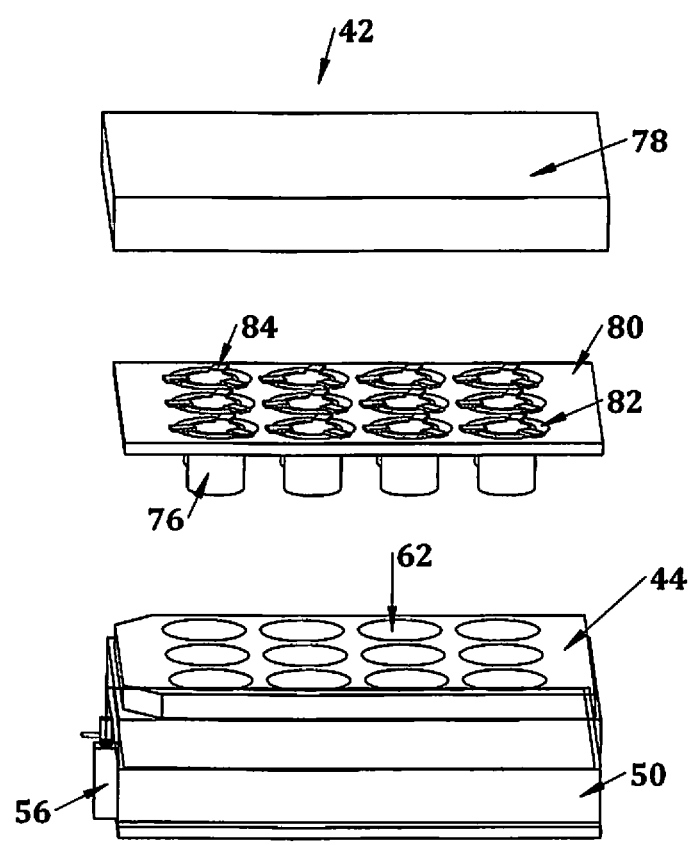
FIG. 3 illustrates an exploded view of the well plate cassette of the system of FIG. 1 with its culture insert carrying plate, inserts, and lid.
Figure 3A:
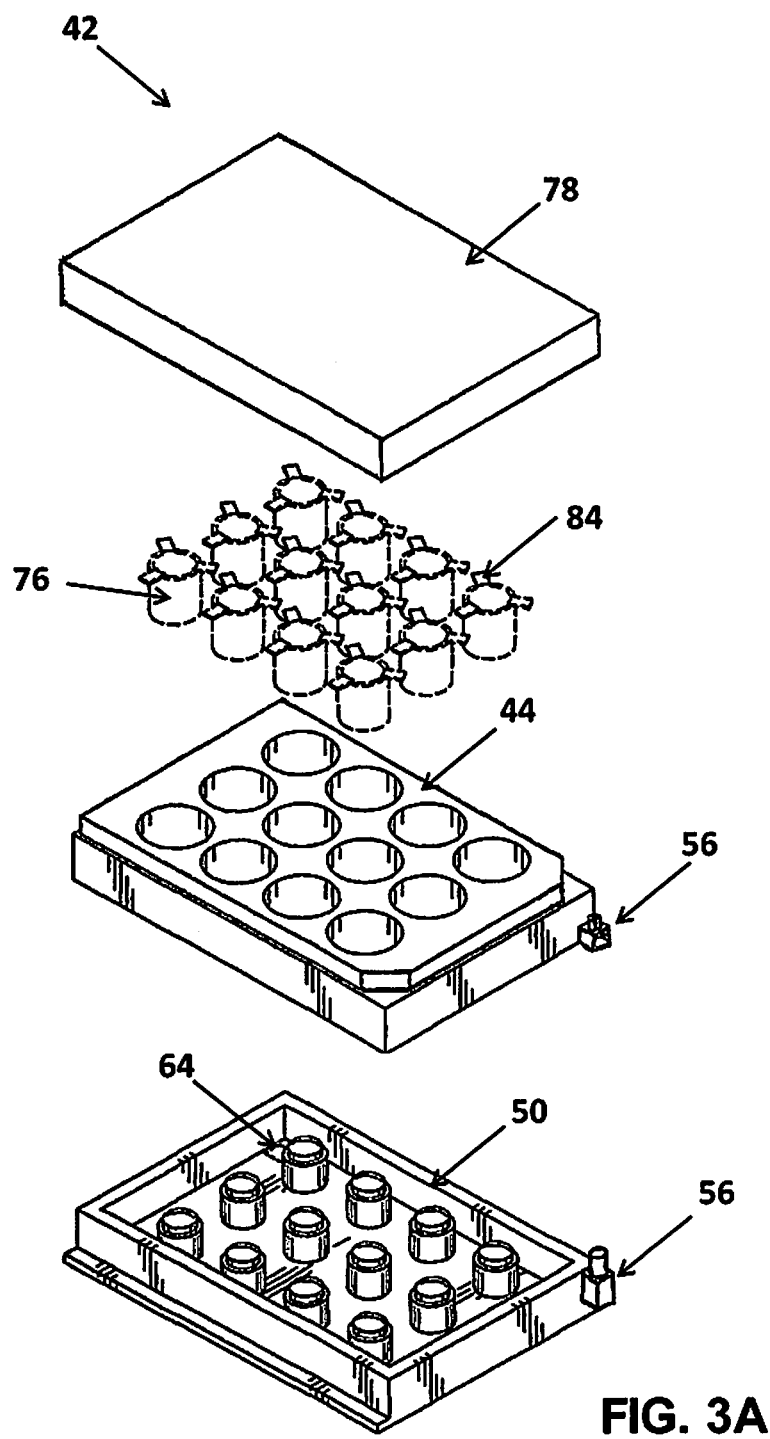
FIG. 3A illustrates an exploded view of an alternative embodiment of the well plate cassette of the system of FIG. 1 with inserts and lid.

In a non-limiting embodiment of the cassette 42, the top plate 44 and its open wells 46, and the base plate 20 are designed to be similar in material (e.g., transparent or semi-transparent polycarbonate), size and shape as standard well plate (e.g., CELLSTAR® Cell Culture Multiwell Plates manufactured by Greiner Bio-One) so that conventional culture inserts 76 and well plate lid 78 can be used with the system 100. An optional culture insert carrying plate 80 with apertures 82 corresponding to positions of the open wells 46, is used to conveniently carry all of the inserts 76 in and out of the well plate cassette 42. Each insert 76 includes hangers 84 that allow the insert 76 to hang from the culture insert carrying plate 80 as shown in FIGS. 3-4. The insert 76 further includes a selectively permeable and semi-transparent filter base 86 as shown in FIGS. 4, 8A and 9A. Please note that the inserts 76 can also be directly placed in and out of the well plate cassette 42 as shown in FIG. 3A without the culture insert carrying plate 80. An exemplary non-limiting embodiment of the insert 76 is ThinCert™ manufactured by Greiner Bio-One. *C. elegans* nematodes are cultured within each insert 76. The filter base 86 allows the desired nematodes to stay within the insert 76 during processing while undesirable waste, nematode eggs, larva, and undersized nematodes are removed during buffer washes.

Figure 11:
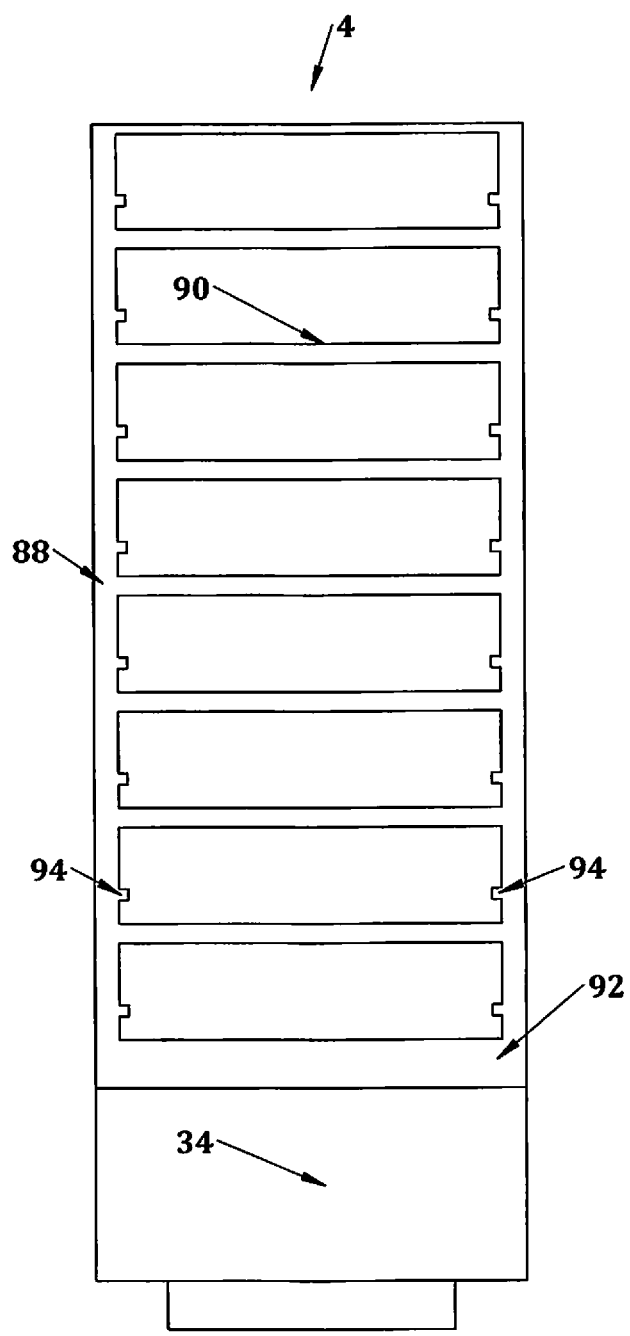
FIG. 11 is a side view of the well plate assembly of the system shown in FIG. 1.

Referring to FIGS. 1 and 11, the wall plate assembly 4 includes a support structure 88 including multiple trays 90 and a support base 92. The support base 92 is attached to the orbital shaker 34. The orbital shaker 34 provides the desired vigorous shaking of the solutions contained in the sealed wells 62 during operation. Each tray 90 includes retaining features 94 configured to interact with cassette retaining features 72 for the purpose of securely holding the cassette 42 within the well plate assembly 4.

Figure 12:
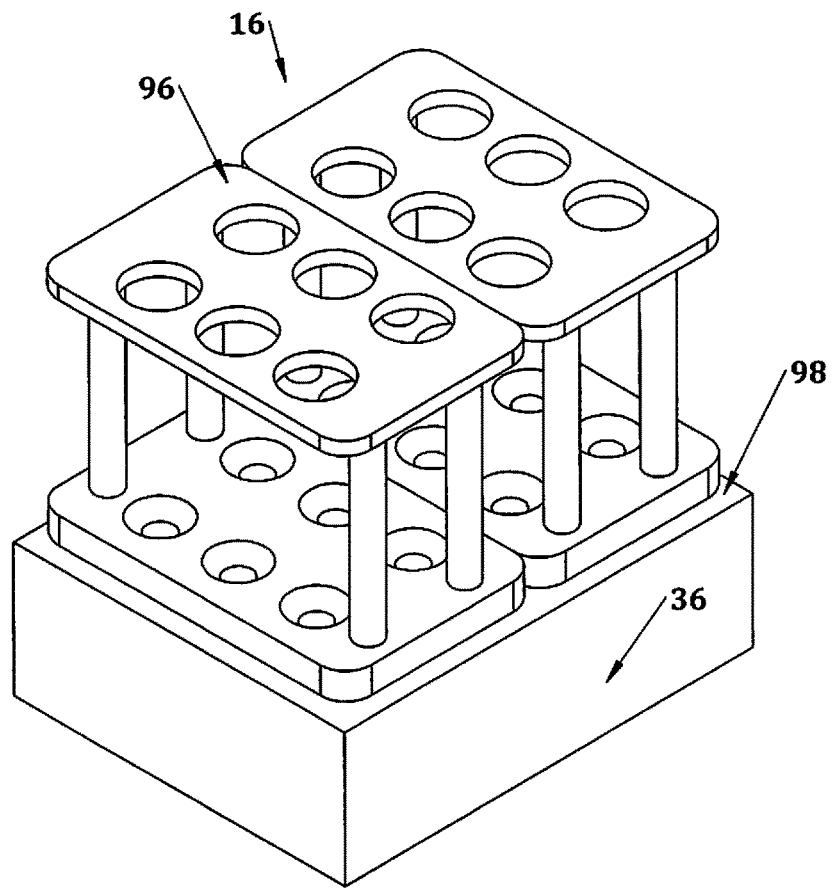
FIG. 12 is a perspective view of the reagent assembly of the system shown in FIG. 1.
Figure 13:
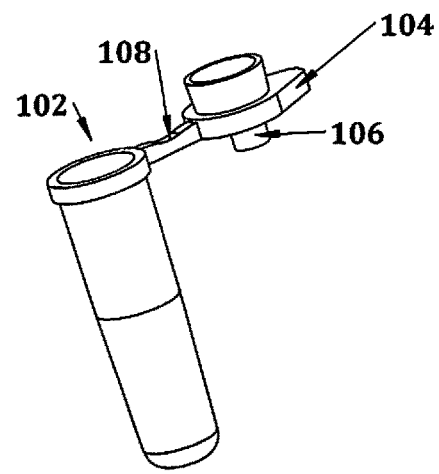
FIG. 13 is a perspective view of the reagent container with its automated lid.

Referring to FIGS. 12-13, the reagent assembly 16 includes a container rack 96 situated on top of a plate 98 of the orbital shaker 36. The container rack 96 is configured to hold the different reagents contained in individual containers 102 desired for a specific experiment. Each individual container 102 is optionally provided with an automated lid 104 controlled by a reagent lid sensor 106 and an automated hinge 108. When the reagent lid sensor 106 receives a predetermined signal from the liquid dispensing lid sensor 106 of the liquid dispensing assembly 12, the reagent lid sensor 106 activates the automated hinge 108 to open the lid 104. When the reagent lid sensor 106 receives a different predetermined signal (including but not limited to a lack of any signal) from the liquid dispensing lid sensor 106 of the liquid dispensing assembly 12, the reagent lid sensor 106 deactivates the automated hinge 108 in order to close the lid 104. The automated lid 104 functions to protect the reagent stored in the container 102 from the external environment and evaporation. Adjacent to the reagent assembly 16 is the pipette tip holder 17. The pipette tip holder 17 holds the pipette tips 112 that are used by the liquid dispensing assembly 12 to aspirate and dispense the reagents contained in the containers 102. In an effort to avoid cross-contamination, there is a corresponding pipette tip 112 stored in the pipette tip holder 17 for each reagent.

Figure 14:
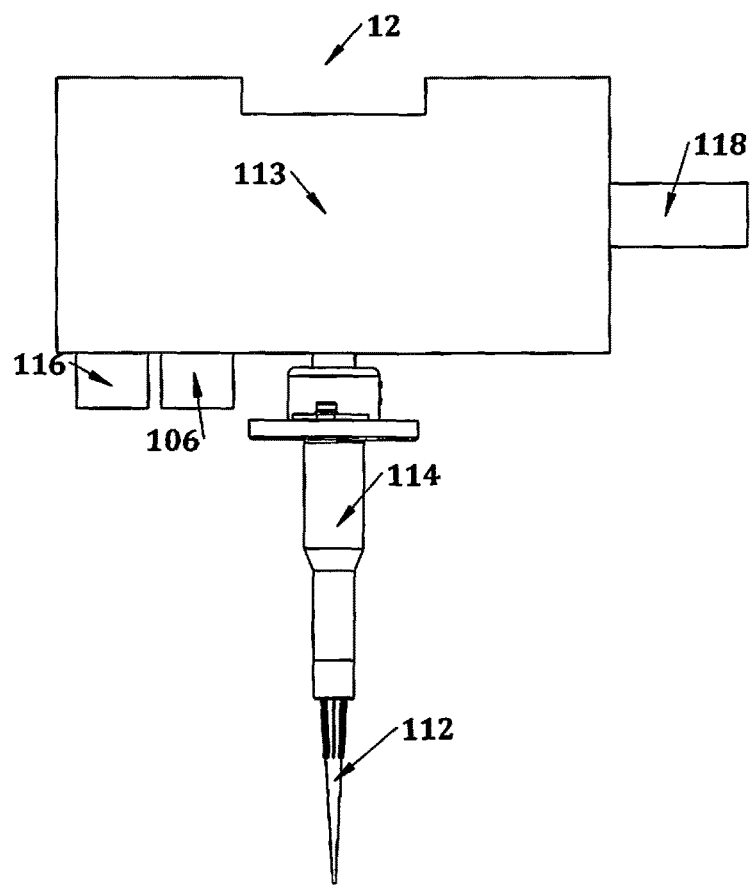
FIG. 14 is a perspective view of the liquid dispensing assembly of the system shown in FIG. 1.

Referring to FIG. 1, each of the two robot arms 8, 10, can independently move in 3 dimensions (x, y, z axis). See e.g., Cavro® Omni Robot manufactured by Tecan Trading AG located in Switzerland. One arm 8 is attached to and moves the liquid dispensing assembly 12 in three axes (x, y, z) to a specific predetermined location. Referring to FIG. 14, the liquid dispensing assembly 12 includes a liquid dispensing housing 113, an automated aspirating and dispensing pipette 114 adapted to accept the pipette tip 112, the liquid dispensing lid sensor 106, a liquid level sensor 116 (e.g., ultrasonic sensor), and a cassette grabber 118.

Figure 15:
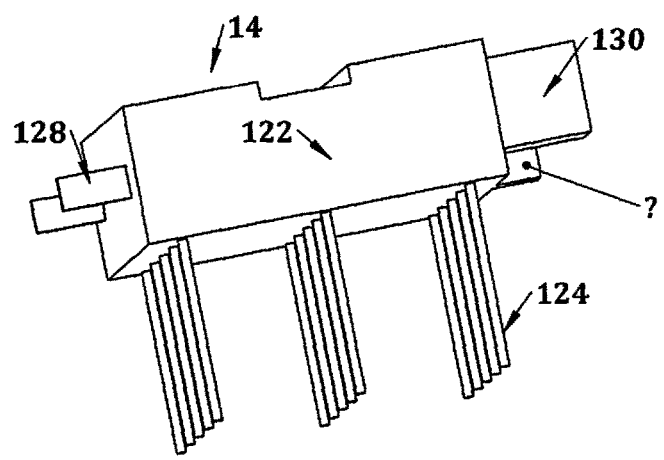
FIG. 15 is a perspective view of the washing and imaging assembly of the system shown in FIG. 1.

Referring to FIGS. 1 and 15, the robot arm 10 is attached to and moves the wash and imaging assembly 14. This assembly (14) includes an interchangeable automated buffer dispensing head 122 in fluid communication with pipette tips 124. The number and spacing of pipette tips 124 correspond with the number and spacing of inserts 76 placed in the designated cassette 42. The dispensing head 122 is also in fluid communication with the buffer container 40 via a buffer conduit (e.g., plastic tubing). The automated buffer dispensing head 122 includes suitable art-disclosed means (e.g., pump) to transfer the buffer from the buffer container 40 to the pipette tips 124. The washing and imaging assembly further includes a cassette grabber 128 and a camera 130.

During operation, the arm 10 moves the wash and imaging assembly 14 in three axes (x, y, z) to a specific predetermined location. For example and referring to FIG. 10, the arm 10 moves the assembly 14 to a location wherein it can activate its cassette grabber 128 to grab and move a designated cassette 42 and its corresponding well plate lid 78 from its corresponding tray 90 to the predetermined position 132 on the washing platform 22 so that the drainage valve 64 is coupled with the drainage coupler 66 and the lever 60 of the spring loaded connector 56 is engaged with the switch controller 71 of the linear actuator 70. The grabber 128 then grabs and moves the lid 78 from the cassette 42 to another predetermined position 134 on the washing platform 22 exposing the sealed wells 62 to the environment. The arm 10 then moves to a predetermined location that allows the pipette tips 124 to dispense buffer solution from the buffer container 40 into all of the inserts 76 located within the cassette 42. Simultaneously, the switch controller 71 causes the bottom openings 49 to decouple from their corresponding well bottoms 52 allowing the used reagents and buffer solutions contained therein to leak out onto the base plate 50 and drains out from the drainage valve 64 and into a waste container 38 via the drainage coupler 66 and the drainage conduit 68. The drainage conduit 68 may optionally include a drainage pump (not shown) to assist in drainage of fluid from the cassette 42 into the waste container 38. This cleaning process causes the buffer solution to flow through each insert 76 cleaning the nematodes and removing waste from the insert 76.

Once the cleaning process is completed, the switch controller 71 causes the bottom openings 49 to couple once again with their corresponding the well bottoms 52 and its sealing feature 54 to form sealed wells 62 that can contain fluid without leakage as shown in FIGS. 8 and 8A. Additional buffer solution is delivered from the pipette tips 112 into the wells 62. The arm 10 then moves the camera 130 into a position where it 130 can take photos of the nematodes inside each insert 76 within the cassette 42. During this imaging process, the wash platform is preferred to be lighted in order to provide better illumination and images. After the imaging process, buffer solutions are once again removed from the wells 62 using the mechanism described above.

Thereafter, the cassette grabber 128 is activated and moved by the arm 10 to grab and place the well plate lid 78 back on the top of the cassette 42. The grabber 128 then grab the cassette 42 and move it back to its original location on its corresponding tray 90 secured by the interaction between retaining features (72, 94).

Subsequently and referring to FIG. 1, the robot arm 8 moves the liquid dispensing assembly 12 to a location wherein it can activate its cassette grabber 118 to grab and move that same cassette 42 and its lid 78 from its tray 90 to the predetermined position 120 on the reagent platform 24. Thereafter the grabber 118 grabs and moves the lid 78 from the cassette 42 to another predetermined position 123 on the reagent platform 24 again exposing the sealed wells 62 to the environment. The arm 8 then move the pipette 114 to a predetermined location in order to couple with a designated pipette tip 112 stored in the pipette tip holder 17. Once the tip 112 is coupled with the pipette 114, the arm 8 moves the pipette 114 to the location of the corresponding container 102 and activates the reagent lid sensor 106 to open the container's automated lid 104. Once the lid 104 is opened, the liquid level sensor 116 detects the reagent level within the container 102 and aspirates a predetermined amount of reagent into the pipette tip 112. Subsequently, the arm 8 moves out of the container 102 and then its reagent lid sensor 106 causes the automated hinge 108 to close the lid 104. The arm 8 then moves the pipette tip 112 to the designated well 62 and dispenses a predetermined amount of reagent into the well 62 before it 112 moves to another designated well 62 for further dispensation of reagent. This reagent dispensing process is repeated for each well 62 that is designated to receive a specific amount of the reagent. Thereafter, the arm 8 moves the pipette 114 to a desired location above the pipette tip's 112 original location within the pipette tip holder 17. The pipette 114 releases the pipette tip 112 back into its location within the pipette tip holder 17. The steps described in this paragraph for aspirating and dispensing reagent from a container 102 to the designated wells 62 are repeated for each desired reagent until all of the wells 62 contain their predetermined amounts of reagents.

Upon completion of the reagent dispensing step, the cassette grabber 118 is activated and moved by the arm 8 to grab and place the well plate lid 78 back on the top of the cassette 42. The grabber 118 then grab the cassette 42 and move it back to its original location on its corresponding tray 90 secured by secured by the interaction between retaining features (72, 94).

During any period when a grabber 118 or 128 is trying to grab and place a cassette 42 in and out of the well plate assembly 4, the well plate orbital shaker 34 is deactivated by the controller 19 and its vigorous shaking is temporary paused until the grabber 188 or 128 is no longer within the well plate assembly 4 zone. During the period when the liquid dispensing assembly 12 is in the process of aspirating and dispensing reagents contained the containers 102, the reagent orbital shaker 36 is deactivated by the controller 19 and its vigorous shaking is temporary paused until the reagent dispensing process is completed.

All of the automated steps and actions, including but not limited to movements of the robot arms (8, 10); the aspiration and dispensation of reagents by the liquid dispensing assembly 12; the opening and closing of each container 102; the dispensation of buffer by the wash and imaging assembly 14; the activation and deactivation of the orbital shakers (34, 36), the linear actuator 56, and the sensors (106, 116); and the imaging of the wells 62 by the camera 130, are all controlled by the controller 19. It is optional to provide additional sensors to assist in the movements of the robot arms (8, 10) and the dispensation of reagents and buffer.

Furthermore, it should be noted that the system 100 allows both robot (8, 10) arms to operate simultaneously to increase throughput. Moreover, additional well plate assembly 4 with additional well plate cassettes 42 can also be added to the system 100 to further increase throughput.

In one non-limiting embodiment, the system 100 fits into a standard sized incubator in order to keep the temperature constant during the entire process. Alternatively, the system 100 may optionally include an incubator (not shown) to house its other components described herein.

The present invention also provides a method of using the system 100 to cultivate transgenic *C. elegans*. The method includes the following steps. First, the method places a predetermined number of well plate cassettes 42 having wells containing *C. elegans* bathing in predetermined bacterial solutions (e.g., for the purpose of their transgenic cultivation) into the well plate assembly 4 with their lids 78 and turns on the well plate orbital shaker 34 to provide desired suitable art-disclosed amount of vigorous shaking for the desired time duration in order to keep the bacteria in suspension within each well. Second, the method turns off the well plate orbital shaker 34 and uses the grabber 128 to remove one of the well plate cassettes 42 and its lid 78 and to place them on the position 132 on the washing platform 22 in such a fashion that the drainage valve 64 couples with the drainage coupler 66 and the level 60 engages with the switch controller 71.

Third, the method uses the grabber 128 to place the lid 78 to the position 134 on the washing platform 22. Fourth, the method activates the switch controller 71 to decouple the bottom openings 49 from their corresponding well bottoms 52 thereby allowing the used reagents and buffer solutions contained therein to leak out onto the base plate 50 and drains out from the drainage valve 64 via the drainage conduit 68 and into a waste container 38. Fifth, the method uses the arm 10 to move the pipette tips 124 over the exposed well plate cassette 42 and dispenses fresh buffer solution from the buffer container 40 into all of the inserts 76 located within the cassette 42. This cleaning process causes the buffer solution to flow through each insert 76 cleaning the *C. elegans* and removing waste from the insert 76. Sixth, once sufficient buffer solutions have been delivered to the *C. elegans* for washing, the switch controller 71 couples the bottom openings 49 with their corresponding well bottoms 52 and the sealing feature 54 to form sealed wells 62. Seven, additional buffer solution is delivered from the pipette tips 112 into the wells 62. Eight, the method uses the arm 10 to move the camera 130 into a position for imaging the *C. elegans* inside each insert 76 within the cassette 42. During this imaging process, the wash platform is preferred to be lighted in order to provide better illumination and images. Ninth, the method removes the buffer solutions from the wells 62 using steps fourth and fifth described above. Tenth, the method activates the cassette grabber 128 to grab and move the well plate lid 78 back on the top of the cassette 42. Eleventh, the grabber 128 then grab the cassette 42 and move it back to its original location on its corresponding tray 90 of the well plate assembly 4. Twelfth, the method activates the grabber 118 to move this cassette and lid 78 from the tray 90 to the position 120 on the reagent platform 24 and then moves the lid 78 to the position 123. Thirteen, the method provides reagents stored in individual containers 102 and maintains the reagents by using the orbital shaker 36 in order to keep the bacteria in suspension within each container 102. Fourteen, the method stops the shaking of the orbital shaker 36 and uses the liquid dispensing assembly 12 to add predetermined fresh bacterial solutions from the containers 102 to each of the designated wells 62 using the process discussed above. Fifteen, the method activates the cassette grabber 118 to grab and move the well plate lid 78 back on the top of the cassette 42. Sixteen, the grabber 118 then grab the cassette 42 and move it back to its original location on its corresponding tray 90 of the well plate assembly 4. Seventeen, the method provides vigorous shaking to the wells 62 and the reagents located within the containers 102. Eighteen, these steps are repeated for all of the cassettes 42 stored in the well plate assembly 4 on predetermined durations of time.

Although the present invention including the system 100 and the method discussed herein are used for cultivation of *C. elegans*, it is not limited to its cultivation transgenic *C. elegans* alone. The present invention, including the system 100 and method discussed herein, is applicable to cultivating and/or experimenting any other suitable microorganisms.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method of using an automated system for cultivating *C. elegans* comprising:
   (a) providing an automated system comprising a housing, a well plate assembly having a self-draining well plate cassette, a liquid dispensing assembly operated by a first three axes positioner, a wash and imaging assembly operated by a second three axis positioner, a reagent assembly, a pipette tip holder, and a controller wherein:
      (i) the cassette includes a lid, a top plate having open wells, a bottom plate having raised well bottoms and sealing features corresponding to locations of the open wells, a spring loaded connector having biasing tension spring and a lever that controls compression and expansion of the biasing tension spring, a self-sealing drainage valve that only drains out fluid upon coupling with a drainage coupler, and culture inserts;

(ii) each of the open wells include a top opening and a bottom opening;

(iii) upon compression of the biasing tension spring by the lever, the bottom openings of the open wells couple with the sealing features of the well bottoms to form sealed wells;

(iv) upon expansion of the biasing tension spring by the lever, the bottom openings decouple from the sealing features of well bottoms allowing any fluid contained in each of the sealed wells of the cassette to leak out onto the bottom plate and to drain out via the drainage valve when the drainage valve is coupled to a drainage coupler of the wash and imaging assembly;

(v) the well plate assembly further includes a first orbital shaker and a support structure having multiple trays and a support base;

(vi) the wash and imaging assembly includes an automated buffer dispensing head designed to accept pipette tips, a first cassette grabber, a camera, a washing platform, a linear actuator having a switch controller, and the drainage coupler;

(vii) the liquid dispensing assembly includes an automated aspiring and dispensing pipette, a liquid dispensing lid sensor, a liquid level sensor, and a second cassette grabber;

(viii) the reagent assembly includes a container rack, at least one reagent container containing a bacterial solution, a reagent platform, and a second orbital shaker activated to shake the at least one reagent container; and (ix) the controller controls operations of the first three axes positioner, the second three axis positioner, the first orbital shaker, the second orbital shaker, the liquid dispensing assembly, the wash and imaging assembly, and the reagent assembly;

(b) placing the cassette onto one of the multiple trays of the support structure of the well plate assembly wherein the culture inserts containing *C. elegans* are bathing in bacterial solutions within the seal wells of the cassette;

(c) activating the first orbital shaker to shake the bacterial solutions;

(d) deactivating the first orbital shaker;

(e) activating the first cassette grabber to transfer the cassette from the support structure to a first predetermined position on the washing platform wherein the drainage valve couples with the drainage coupler, and the lever engages with the switch controller allowing the linear actuator to control the lever's ability to cause compression or expansion of the biasing tension spring;

(f) activating the first cassette grabber to transfer the lid from the cassette to a second predetermined position on the washing platform;

(g) activating the linear actuator to cause expansion of the biasing tension spring by the lever resulting in decoupling of the bottom openings from the sealing features and leakage of the bacterial solutions out of the cassette via the drainage valve and the drainage coupler;

(h) activating the automated buffer dispensing head to dispense buffer solution into the culture inserts allowing the buffer solution to flow through the culture inserts thereby cleaning the *C. elegans* and removing waste from the culture inserts;

(i) activating the linear actuator to cause compression of the biasing tension spring by the lever resulting in coupling of the bottom openings with the sealing features to form the sealed wells containing the culture inserts with the *C. elegans* and the buffer solution;

(j) deactivating the automated buffer dispensing head to stop the dispensation of the buffer solution into the culture inserts;

(k) imaging the *C. elegans* with the camera;

(l) activating the linear actuator to cause expansion of the biasing tension spring by the lever resulting in decoupling of the bottom openings from the sealing features and leakage of the buffer solution onto the bottom plate and drainage of the buffer solution out of the cassette via the drainage valve and the drainage coupler (m) activating the linear actuator to cause compression of the biasing tension spring by the lever resulting in coupling of the bottom openings with the sealing features to form the sealed wells containing the culture inserts with the *C. elegans*;

(n) activating the first cassette grabber to transfer the lid from the second predetermined position on the washing platform back to the cassette;

(o) activating the first cassette grabber to transfer the cassette from the washing platform to one of the multiple trays of the support structure;

(p) activating the second cassette grabber to transfer the cassette from the support structure to a third predetermined position on the reagent platform;

(q) activating the second cassette grabber to transfer the lid from the cassette to a fourth predetermined position on the reagent platform;

(r) deactivating the second orbital shaker;

(s) activating the automated aspiring and dispensing pipette of the liquid dispensing assembly to transfer a predetermined amount of bacterial solution from the reagent assembly to each of the sealed wells of the cassette;

(t) activating the second orbital shaker;

(u) activating the second cassette grabber to transfer the lid from the fourth predetermined position on the reagent platform back to the cassette;

(v) activating the second cassette grabber to transfer the cassette from the reagent platform to one of the multiple trays of the support structure; and (w) activating the first orbital shaker.

2. The method of claim 1 wherein the automated system further includes one or more additional self-draining well plate cassettes; and the method further includes repeating steps (b) through (w) for each of the additional cassettes.

3. The method of claim 1 wherein the steps (b) through (w) are repeated multiple times until the *C. elegans* have reached a desired cultivated growth stage.

4. The method of claim 1 wherein diameter of the bottom opening is smaller than diameter of the top opening.

5. The method of claim 1 wherein the sealing feature is a silicone surface.

6. The method of claim 1 wherein the sealing feature is at least one O-ring.

7. The method of claim 1 wherein the cassette further includes a culture insert carrying plate.

8. The method of claim 1 wherein the method is used to cultivate transgenic *C. elegans*.

9. The method of claim 1 wherein:

(i) the at least one reagent container includes an automated lid controlled by a reagent lid sensor and an automated hinge;

(ii) when the reagent lid sensor receives a first predetermined signal from the liquid dispensing lid sensor, the reagent lid sensor activates the automated hinge to open the automated lid; and (iii) when the reagent lid sensor receives a second predetermine signal from the liquid dispensing lid sensor, the reagent lid sensor deactivates the automated hinge in order to close the automated lid.

10. A method of using an automated system for cultivating *C. elegans* comprising:

(a) providing an automated system comprising a housing, a well plate assembly having more than one self-draining cassettes, a liquid dispensing assembly operated by a first three axes positioner, a wash and imaging assembly operated by a second three axis positioner, a reagent assembly, a pipette tip holder, and a controller wherein:

(i) each of the cassettes includes a lid, a top plate having open wells, a bottom plate having raised well bottoms and sealing features corresponding to locations of the open wells, a spring loaded connector having biasing tension spring and a lever that controls compression and expansion of the biasing tension spring, a self-sealing drainage valve that only drains out fluid upon coupling with a drainage coupler, and culture inserts;

(ii) each of the open wells includes a top opening and a bottom opening;

(iii) upon compression of the biasing tension spring by the lever, the bottom openings of the open wells couple with the sealing features of the well bottoms to form sealed wells;

(iv) upon expansion of the biasing tension spring by the lever, the bottom openings decouple from the sealing features of well bottoms allowing any fluid contained in each of the sealed wells to leak out onto the bottom plate and to drain out via the drainage valve when the drainage valve is coupled to a drainage coupler of the wash and imaging assembly;

(v) the well plate assembly further includes a first orbital shaker and a support structure having multiple trays and a support base;

(vi) the wash and imaging assembly includes an automated buffer dispensing head designed to accept pipette tips, a first cassette grabber, a camera, a washing platform, a linear actuator having a switch controller, and the drainage coupler;

(vii) the liquid dispensing assembly includes an automated aspiring and dispensing pipette, a liquid dispensing lid sensor, a liquid level sensor, and a second cassette grabber;

(viii) the reagent assembly includes a container rack, at least one reagent container containing a bacterial solution, a reagent platform, and a second orbital shaker activated to shake the at least one reagent container; and (ix) the controller controls operations of the first three axes positioner, the second three axis positioner, the first orbital shaker, the second orbital shaker, the liquid dispensing assembly, the wash and imaging assembly, and the reagent assembly;

(b) placing the cassettes onto the multiple trays of the support structure of the well plate assembly wherein the culture inserts containing *C. elegans* are bathing in bacterial solutions within the seal wells of each of the cassettes and performing the following steps for each of the cassettes;

(c) activating the first orbital shaker to shake the bacterial solutions;

(d) deactivating the first orbital shaker;

(e) activating the first cassette grabber to transfer one of the cassettes from the support structure to a first predetermined position on the washing platform wherein the drainage valve couples with the drainage coupler, and the lever engages with the switch controller allowing the linear actuator to control the lever's ability to cause compression or expansion of the biasing tension spring;

(f) activating the first cassette grabber to transfer the lid from the cassette to a second predetermined position on the washing platform;

(g) activating the linear actuator to cause expansion of the biasing tension spring by the lever resulting in decoupling of the bottom openings from the sealing features and leakage of the bacterial solutions out of the cassette via the drainage valve and the drainage coupler;

(h) activating the automated buffer dispensing head to dispense buffer solution into the culture inserts allowing the buffer solution to flow through the culture inserts thereby cleaning the *C. elegans* and removing waste from the culture inserts;

(i) activating the linear actuator to cause compression of the biasing tension spring by the lever resulting in coupling of the bottom openings with the sealing features to form the sealed wells containing the culture inserts with the *C. elegans* and the buffer solution;

(j) deactivating the automated buffer dispensing head to stop the dispensation of the buffer solution into the culture inserts;

(k) imaging the *C. elegans* with the camera;

(l) activating the linear actuator to cause expansion of the biasing tension spring by the lever resulting in decoupling of the bottom openings from the sealing features and leakage of the buffer solution onto the bottom plate and drainage of the buffer solution out of the cassette via the drainage valve and the drainage coupler (m) activating the linear actuator to cause compression of the biasing tension spring by the lever resulting in coupling of the bottom openings with the sealing features to form the sealed wells containing the culture inserts with the *C. elegans;*

(n) activating the first cassette grabber to transfer the lid from the second predetermined position on the washing platform back to the cassette;

(o) activating the first cassette grabber to transfer the cassette from the washing platform to one of the multiple trays of the support structure;

(p) activating the second cassette grabber to transfer the cassette from the support structure to a third predetermined position on the reagent platform;

(q) activating the second cassette grabber to transfer the lid from the cassette to a fourth predetermined position on the reagent platform;

(r) deactivating the second orbital shaker;

(s) activating the automated aspiring and dispensing pipette of the liquid dispensing assembly to transfer a predetermined amount of bacterial solution from the reagent assembly to each of the sealed wells of the cassette;

(t) activating the second orbital shaker;

(u) activating the second cassette grabber to transfer the lid from the fourth predetermined position on the reagent platform back to the cassette;

(v) activating the second cassette grabber to transfer the cassette from the reagent platform to one of the multiple trays of the support structure; and (w) activating the first orbital shaker.

11. The method of claim 10 wherein the steps (b) through (w) are repeated multiple times until the *C. elegans* have reached a desired cultivated growth stage.

12. The method of claim 10 wherein diameter of the bottom opening is smaller than diameter of the top opening.

13. The method of claim 10 wherein the sealing feature is a silicone surface.

14. The method of claim 10 wherein the sealing feature is at least one O-ring.

15. The method of claim 10 wherein each of the cassettes further includes a culture insert carrying plate.

16. The method of claim 10 wherein:

(i) the at least one reagent container includes an automated lid controlled by a reagent lid sensor and an automated hinge;

(ii) when the reagent lid sensor receives a first predetermined signal from the liquid dispensing lid sensor, the reagent lid sensor activates the automated hinge to open the automated lid; and (iii) when the reagent lid sensor receives a second predetermine signal from the liquid dispensing lid sensor, the reagent lid sensor deactivates the automated hinge in order to close the automated lid.

17. The method of claim 10 wherein the method is used to cultivate transgenic *C. elegans*.

\* \* \* \* \*